(12) United States Patent
Edelman et al.

(10) Patent No.: US 6,375,648 B1
(45) Date of Patent: *Apr. 23, 2002

(54) INFILTRATION CANNULA WITH TEFLON COATED OUTER SURFACE

(75) Inventors: William Edelman, Sharon, MA (US); John C. Brumbach, Chicago, IL (US)

(73) Assignee: Misonix Incorporated, Farmingdale, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,940

(22) Filed: Oct. 2, 1998

(51) Int. Cl.⁷ .............................................. A61M 1/00
(52) U.S. Cl. ....................................... 604/542; 604/265
(58) Field of Search ................................ 604/264, 265, 604/280, 523, 524–527, 151, 272–274, 266, 540, 541, 542, 19, 48, 22

(56) References Cited

U.S. PATENT DOCUMENTS

| | | | |
|---|---|---|---|
| 4,327,709 A | 5/1982 | Hanson et al. ............... 128/1 D |
| 4,681,106 A | 7/1987 | Kensey et al. ............... 128/305 |
| 4,728,319 A | 3/1988 | Masch .......................... 604/22 |
| 4,736,733 A | * 4/1988 | Adair .......................... 604/280 |
| 4,769,005 A | * 9/1988 | Ginsburg et al. |
| 4,775,365 A | 10/1988 | Swartz ........................ 604/119 |
| 4,792,327 A | 12/1988 | Swartz ........................ 604/22 |
| 4,795,426 A | 1/1989 | Jones ........................... 604/51 |
| 4,815,462 A | 3/1989 | Clark ........................... 128/305 |
| 4,886,491 A | 12/1989 | Parisi et al. ................... 604/22 |
| 4,898,575 A | 2/1990 | Fischell et al. ................ 604/22 |
| 4,932,935 A | 6/1990 | Swartz ........................ 604/22 |
| 5,112,302 A | 5/1992 | Cucin .......................... 604/35 |
| 5,158,086 A | 10/1992 | Brown et al. .......... 128/662.03 |
| 5,178,158 A | * 1/1993 | De Toledo |
| 5,195,988 A | 3/1993 | Haaga .......................... 604/265 |
| 5,236,414 A | 8/1993 | Takaso ......................... 604/22 |
| 5,312,328 A | 5/1994 | Nita et al. ..................... 604/22 |
| 5,348,535 A | 9/1994 | Cucin .......................... 604/35 |
| 5,368,035 A | 11/1994 | Hamm et al. .......... 128/662.06 |
| 5,405,318 A | 4/1995 | Nita ............................ 604/22 |
| 5,464,016 A | 11/1995 | Nicholas et al. ........ 128/662.06 |
| 5,520,189 A | 5/1996 | Malinowski et al. ... 128/662.03 |
| 5,643,198 A | 7/1997 | Cucin .......................... 604/22 |
| 5,730,742 A | 3/1998 | Wojciechowicz ............ 606/49 |
| 5,766,194 A | * 6/1998 | Smith |
| 5,817,050 A | * 10/1998 | Klein |

FOREIGN PATENT DOCUMENTS

| DE | 386408 | * 1/1990 | |
|---|---|---|---|
| EP | 0 189 329 | 7/1986 | ........... A61B/17/22 |
| WO | WO 91/14401 | 10/1991 | ........... A61B/8/12 |

* cited by examiner

*Primary Examiner*—Sharon Kennedy
*Assistant Examiner*—LoAn H. Thanh
(74) *Attorney, Agent, or Firm*—Welsh & Katz, Ltd.

(57) ABSTRACT

An infiltration cannula is provided. The infiltration cannula includes an axially elongated tube having a circular cross-section, a proximal end portion adapted to receive a treatment fluid and a distal end portion with a plurality of apertures disposed in a transverse sidewall of the distal end portion of the elongated tube for dispensing the treatment fluid. The cannula also includes a teflon coating disposed over and outer surface of the elongated member.

13 Claims, 1 Drawing Sheet

INFILTRATION CANNULA WITH TEFLON COATED OUTER SURFACE

BACKGROUND OF THE INVENTION

1. Field of the Invention

Figure 1:
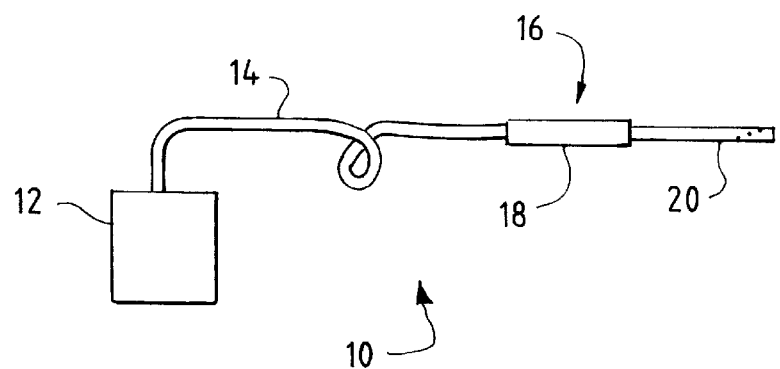

The present invention relates to devices used with ultrasonic cutting devices used in the removal of tissue and/or matter from a living body, and more particularly, to an improved infiltration cannula which is capable of infusing tissue with medication.

2. Description of Related Art

Probes or scalpels for the fragmentation and removal of materials, tissue and fluids from living beings are known to the art. For example, U.S. Pat. No. 2,227,727, issued Jan. 7, 1941 to Vincent Leggiardro, discloses an apparatus for fragmenting naturally formed stones, such as kidney stones, and the like, utilizing a high speed reciprocating rod which may have a blunt end, a sharp or chisel point, a cutting blade, or combination thereof, such as a cutting blade having a blunt end.

A particular arrangement in an ultrasonically vibrated surgical tool using an irrigation fluid and an anti-coagulant is disclosed in U.S. Pat. No. 4,493,694, issued Jan. 15, 1985, to David G. Wuchinich, utilizes a hollow tool having a suction passage and at least one pre-aspirating orifice in the wall of the tool, and a plastic sleeve concentrically spaced about the tool for admitting fluid from a supply into the space between the tool and passing substantially all of the fluid through the pre-aspirating orifice.

In the application of ultrasonics to liposuction, instruments of varying configurations recently have been proposed. In U.S. Pat. No. 5,236,414, issued Aug. 17, 1993 to Katsuya Takasu, a tubular body defining a suction passage has an opening in its front lower end, and an outer tube having a corresponding opening, by means of which fat tissue is crushed and/or emulsified due to the vibration of the front end of the tubular body and is then aspirated. In U.S. Pat. No. 5,514,086, issued May 7, 1996, to Parisi et al., an ultrasonically vibrated hollow probe has a port in its surface for aspiration and a tip substantially formed of plastic.

While the use of ultrasonic probes for liposuction has proven effective, it is fraught with discomfort and certain health risks. For example, the ultrasonic removal of tissue may cause pain and swelling. Excessive bleeding may also result from liposuction.

Epinephrine has been found to be effective in reducing bleeding during liposuction. Similarly, Lidocane has been found effective in reducing pain. However, it is often difficult to effectively introduce these drugs into fat tissue, in advance of liposuction.

While prior art devices have relied upon localized injection methods, the process of localized injection may result in a great deal of discomfort. Accordingly, a need exists for a device for infiltrating fat with medication that is less painful to administer and which reduces trauma to tissue.

SUMMARY

An infiltration cannula is provided. The infiltration cannula includes an axially elongated tube having a circular cross-section, a proximal end portion adapted to receive a treatment fluid and a distal end portion with a plurality of apertures disposed in a transverse sidewall of the distal end portion of the elongated tube for dispensing the treatment fluid. The cannula also includes a TEFLON polytetrafluroethylene, PTFE, etc. coating disposed over and outer surface of the elongated member.

BRIEF DESCRIPTION OG THE DRAWINGS

Figure 2A:
Figure 2B:
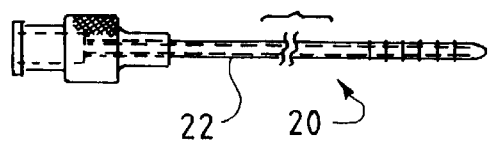
Figure 2C:

FIG. 1 is a block diagram of an infiltration cannula in accordance with an embodiment of the invention;

FIGS. 2a–c are side and end views of a probe of the cannula of FIG. 1; and

Figure 3A:
Figure 3B:
Figure 3C:

FIGS. 3a–c are side and end view of a probe of the cannula of FIG. 1, under an alternate embodiment.

DETAILED DESCRIPTION OF A PREFERRED EMBODIMENT

FIG. 1 depicts an infiltration cannula system 10, generally, in accordance with an illustrated embodiment of the invention. Such cannula system 10 may be used for any of a number of medical procedures (e.g., to prepare a patient for liposuction). Where used for liposuction, the cannula may be used to introduce certain preparatory drugs into a patient's tissue in preparation for emulsification and removal of fat.

Under the procedure, a surgeon makes a small incision in the skin of a patient. A cannula 20 of the cannula system 10 may be inserted through the incision into subcutaneous tissue of the patent and into the underlying fat. Once within the tissue of a patent a treatment solution may be infused into the tissue by working the cannula 20 through the fat tissue of the patient.

Under the embodiment, the cannula system 10 may include a peristaltic pump 18, which provides the treatment solution (e.g., a saline solution of epinephrine and lidocaine to the cannula 20. A reservoir 12 serves as a source of the treatment solution through an interconnecting tube 14.

FIGS. 2a–c are side and end views of a cannula 20 of the cannula system 10. As shown, the cannula 20 may be fabricated of an elongated tube and luers connector. The elongated tube may be fabricated of a number of tubing materials (e.g., stainless steel), having a nominal wall diameter of 2–3 mm and a wall thickness of 0.010 inches.

Under one preferred embodiment, the tube may be fabricated of 2 mm tubing having an outside diameter (OD) of 0.082–0.084 inches and an inside diameter (ID) of 0.061–0.065 inches. Under another embodiment, the tube may be fabricated of 3 mm tubing having an OD of 0.082–0.084 inches and an ID of 0.061–0.065 inches.

An outer surface of the cannula 20 of the cannula system 10 may be coated with a relatively thin layer 22 (e.g., 2–3 mills) of TEFLON (e.g., polytetrafluoroethylene, PTFE, etc.). Coating may be accomplished by any known method.

Coating the cannula 20 with the TEFLON layer 22 has been found to produce unexpected benefits in terms of reduced damage to human tissue. The reduced damage is believed to accrue from the care by which the TEFLON coated cannula 10 slides through fat.

In order to facilitate the infiltration of the treatment fluid, a number of apertures are provided around the periphery of the tube, within a distal end portion of the tube. A relatively even distribution of apertures may be achieved by locating the apertures along a helical line extending from the distal end of the tube towards a near end of the distal portion. For example, the helix of such line may be advanced at a rate of 0.100 inches per revolution and apertures may be located every 60 degrees along that helix as shown in FIG. 2.

Further, to facilitate infusion of tissue with treatment fluids, the cannula 20 may be fabricated of any of a number of lengths. For example, for easily accessible regions the cannula 20 may be fabricated of a relatively short length of 6.2 cm. For more difficult areas needing greater length a longer tube of 12.1 cm may be used.

In another embodiment of the invention (FIG. 3), the tube 20 may be fabricated having a bend for lateral insertions. For example a relatively long region (e.g., 27 cm) may be provided where the distance between incisions is relatively large. A slight bend (e.g., 20 degrees) may be provided separating the relatively long region from a relatively short region (e.g., 8 cm). The relatively short region may be provided with a luer connection for attachment to the handpiece of the pump 18.

Fabricating the cannula system 10 using the relatively long probe allows for the infusion of relatively large areas with treatment solution using fewer incisions. Further, the bend separating the relatively long region from the relatively short region allows greater dexterity in manipulating the cannula 20 in difficult areas.

While particular embodiments of the injection cannula of the invention have been shown and described, it will be appreciated by those skilled in the art that changes and modifications may be made thereto without departing from the invention in its broader aspects and as set forth in the following claims.

What is claimed is:

1. An infiltration cannula for dispensing a treatment fluid comprising:
   - an axially elongated rigid tube of the infiltration cannula with a single annular wall, a proximal end portion adapted to receive the treatment fluid and a distal end portion;
   - a polytetrafluorethylene coating disposed over substantially an entire outer surface of the axially elongated rigid tube; and
   - a plurality of apertures disposed in a transverse sidewall and extending through the sidewall and polytetrafluorethylene coating of the distal end portion of the elongated tube for dispensing the treatment fluid.

2. The infiltration cannula as in claim 1 wherein the elongated tube further comprises stainless steel.

3. The infiltration cannula as in claim 2 wherein the stainless steel tube further comprises a nominal wall thickness of 0.010 inch.

4. The infiltration cannula as in claim 2 wherein the stainless steel tube further comprises a nominal overall diameter of 0.083 inch.

5. The infiltration cannula as in claim 2 wherein the stainless steel tube further comprises a nominal overall diameter of 0.120 inch.

6. The infiltration cannula as in claim 1 wherein the plurality of apertures further comprises a line of apertures where the line defines a helix beginning on the distal end of elongated tube and extending to a near end of the distal end portion.

7. The infiltration cannula as in claim 6 wherein the line of the helix further comprises a spacing of approximately two-tenths of an inch between adjacent loops of the helix.

8. The infiltration cannula as in claim 6 wherein the plurality of apertures along the helix further comprises a sixty degree angular offset between adjacent apertures.

9. The infiltration cannula as in claim 1 further comprising a peristaltic pump coupled to the proximal end of the elongated tube which provides the treatment fluid.

10. The infiltration cannula as in claim 1 wherein the plurality of apertures further comprises a line of apertures on opposing sides of the elongated tube extending from the distal end of the tube to a near end of the distal portion.

11. The infiltration cannula for dispensing a treatment fluid as in claim 1 further comprising a saline solution.

12. The infiltration cannula for dispensing a treatment fluid as in claim 1 further comprising epinephrine.

13. The infiltration cannula for dispensing a treatment fluid as in claim 1 further comprising lidocaine.

* * * * *